United States Patent [19]

Iwatsuki et al.

[11] Patent Number: 4,818,291

[45] Date of Patent: Apr. 4, 1989

[54] SILK-FIBROIN AND HUMAN-FIBRINOGEN ADHESIVE COMPOSITION

[75] Inventors: Makoto Iwatsuki, Tokyo; Toshio Hayashi, Kyoto, both of Japan

[73] Assignee: Ajinomoto Co., Inc., Tokyo, Japan

[21] Appl. No.: 131,427

[22] Filed: Dec. 10, 1987

[30] Foreign Application Priority Data

Dec. 10, 1986 [JP] Japan .................................. 61-294148

[51] Int. Cl.$^4$ ............................................. C08L 89/00
[52] U.S. Cl. ..................................... 106/124; 424/101
[58] Field of Search ........................ 106/124; 530/353; 424/101

[56] References Cited

U.S. PATENT DOCUMENTS 4,414,976  11/1983  Schwartz et al. .................... 106/124

OTHER PUBLICATIONS

Chem. Abstract 54:15,855b, Muller, 1958.

Primary Examiner—Theodore Morris
Attorney, Agent, or Firm—Oblon, Fisher, Spivak, McClelland & Maier

[57] ABSTRACT

The present invention provides a novel adhesive which contains a mixture of human-fibrinogen and silk-fibroin and which is suitable especially for use in surgery. The mixing ratio of silk-fibroin to human-fibrinogen is 5 to 90, preferably 20 to 70% by weight.

4 Claims, 1 Drawing Sheet

SILK-FIBROIN AND HUMAN-FIBRINOGEN ADHESIVE COMPOSITION

BACKGROUND OF THE INVENTION

1. Field of the Invention

The present invention relates to a novel adhesive. More particularly, the present invention relates to a surgical adhesive which is usable in surgical repair of, for example, tissues and is useful for adhesion of tissues and repair and reinforcement of tissues which become frail due to aging.

2. Description of the Related Art

As a surgical adhesive which has been put to practical use, (1) a cyanoacrylate adhesive such as an ethyl 2-cyanoacrylate adhesive and an isobutyl 2-cyanoacrylate adhesive is known. Among these, only the ethyl 2-cyanoacrylate adhesive "Aron Alpha A Sankyo" (registered trade name; produced by Sankyo Company, Limited) has been put on the market a medical product in Japan.

In addition to (1), there is (2) a human-fibrinogen adhesive which utilizes the coagulation of fibrinogen, and kits of "Fibrinogen-Midori" and "Thrombin-Midori" (produced by Green Cross Corporation) are commercially available.

A cyanoacrylate adhesive is a synthetic polymer which is completely heterogeneous with respect to a living body, so that when it is applied to a living body, the tissues on the adherend surface die. The adhesive applied remains for a long time, and it takes one year or more for the adhesive to disappear. In addition, the adhesive obstructs the regeneration of the tissues on the adherend surface extending to the cicatrix. The adherend surface is unfavorably hardened.

On the other hand, a human-fibrinogen adhesive is used as a blood coagulating agent, and when it is used as a surgical adhesive, it is often the case that since the adhesive force is insufficient, several portions must be sutured before applying the adhesive. In other words, the adhesive serves only as a filler of the adherend surfaces.

Accordingly, there is a strong demand for development of an adhesive which has good compatibility with a living organism and has both a practically adequate adhesive force and an immediate adhesive effect.

SUMMARY OF THE INVENTION

As a result of the studies by the present inventors on how to solve the above-described problems, it has been found that an adhesive containing a mixture of human fibrinogen and silk-fibroin as a base material can achieve the above-described aim. The present invention has been accomplished on the basis of this finding.

The present invention provides a novel adhesive which contains a mixture of human-fibrinogen and silk-fibroin and which is suitable especially for use in surgery. The mixing ratio of silk-fibroin to human-fibrinogen is 5 to 90, preferably 20 to 70% by weight.

DETAILED DESCRIPTION OF THE PREFERRED EMBODIMENTS

Figure 1:
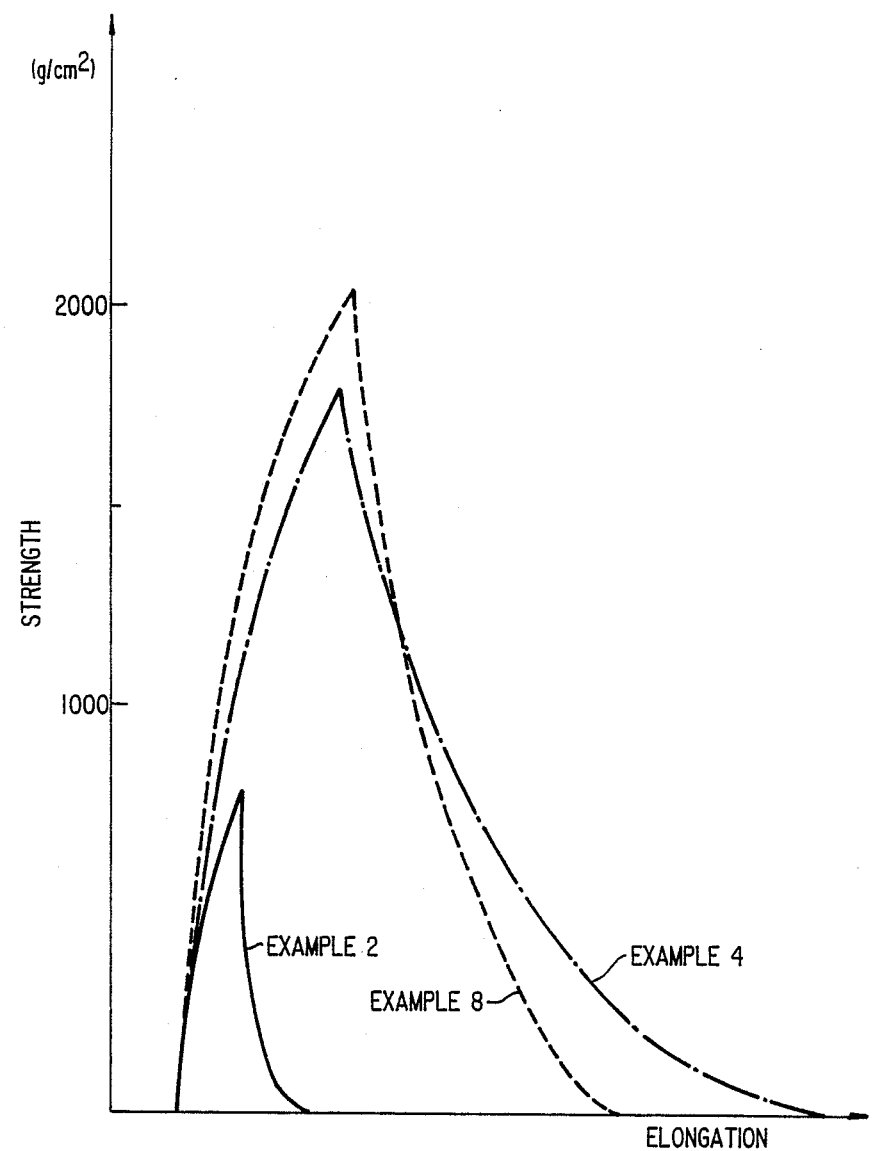
FIG. 1 is a part of the strength-elongation curves obtained by the tests of adhesive strength under shear in the examples.

A silk fiber was approved as a suturing fiber for medical use and has long been in practical use as a non-absorbent suturing fiber. Very few silk fibers are decomposed in a living organism and absorbed thereby, but since a silk fiber is itself a kind of protein, when it is used as a suturing fiber, it has good compatibility with a living body and does not affect any tissues surrounding the silk fiber.

A silk fiber is composed only of fibroin. Fibroin is a fibrous protein in which fibers are easily oriented to each other and crystallized. Fibrous and filmy molded products based on silk fibers have excellent mechanical properties.

Silk-fibroin easily dissolves in a saturated aqueous solution of an inorganic salt such as lithium bromide. By desalting such a solution by dialysis, an aqueous solution of silk-fibroin is obtained.

An aqueous solution of silk-fibroin is characterized in that fibroin molecules are dispersed randomly constituting an $\alpha$-helix structure, and these molecules are easily oriented by a physical stimulus such as vibration and agitation so as to have a $\beta$-zigzag structure and to be insolubilized (a regenerated silk-fibroin molded product is gradually decomposed by enzymes in vivo until it disappears).

The present inventors took notice of the following characteristics of silk-fibroin: (1) it has a good compatibility with a living organism, (2) a molded product of silk-fibroin has excellent mechanical properties, and (3) it is possible to obtain an aqueous solution from silk-fibroin and the solution is easy to render insolubilized and separated by a physical stimulus, and introduced silk-fibroin into a surgical adhesive.

More specifically, a surgical adhesive having good compatibility with a living organism and a strong adhesive force has been invented by utilizing the good adhesiveness of human-fibrinogen with tissues and compensating for its insufficient flexibility, frailness and insufficient strength by the excellent mechanical properties of silk-fibroin, in other words, by compounding human-fibrinogen with silk fibroin.

As the silk material of the silk-fibroin used in the present invention, cocoon silk, waste cocoon, silk waste, bisu, kiki, waste silk cloth, bullet and so forth are used. Bisu and kiki are kinds of silk waste produced in a process of silk-reeling. Bullet is a kind of silk waste produced in a process of silk spinning. Silk-fibroin is obtained by removing sericin from the silk by an ordinary method in warm water in the presence of an activator, if necessary, or in water of room temperature in the presence of an enzyme, and the remaining silk fibroin alone is dried before use. As the silk material of silk-fibroin, domestic silk and wild silk, or a mixture thereof, can be used.

The thus-obtained silk-fibroin is added to an aqueous solution containing ordinarily 5 to 80 wt % of alkali metal salt or alkaline earth metal salt, and dissolved therein under heating and stirring, if necessary.

The alkali metal salts or alkaline earth metal salts usable in the present invention are, for example, LiCl, LiBr, NaI, LiNO$_3$, MgCl$_2$, MgBr$_2$, Mg(NO$_3$)$_2$ and ZnCl$_2$. The concentration of the alkali metal salt or alkaline earth metal salt is 5 to 80 wt %. The ratio of liquid to the silk fibroin is ordinarily 2 to 50 times.

The metal salt is almost completely removed from the thus-obtained silk-fibroin solution by using a dialysis membrane such as by a cellophane film, or by a dialyzer using hollow fibers to obtain an aqueous silk-fibroin solution.

Human-fibrinogen may be obtained by separating it from blood, but since the procedure and the operation are complicated, commercially available "Fibrinogen-Midori" (produced by Green Cross Corporation) may be advantageously used.

When silk-fibroin is mixed with human-fibrinogen, a predetermined amount of distilled water of 32° to 35° C. is first added to human-fibrinogen to dissolve the latter in the former and to obtain an aqueous human-fibrinogen solution. A predetermined amount of aqueous silk-fibroin solution is gently added to and mixed with the aqueous human-fibrinogen solution. An aqueous solution of a mixture of silk-fibroin is unstable, and if violent vibration is applied thereto during handling or preservation, it is insolubilized and separated. To prevent this, silk-fibroin is treated with an enzyme such as chymotrypsin so as to enhance the water-solubility, or a salt which does not affect an organism such as calcium chloride is added to an aqueous solution of a mixture of silk-fibroin so as to enhance the solubility and stability, thereby facilitating handling.

An aqueous solution of a mixture of silk-fibroin is insolubilized when it is freeze-dried, but the above-described ones having a water-solubility enhanced by enzyme treatment or addition of a salt dissolved in distilled water even after freeze-drying, thereby facilitating the preservation, sterilization, etc., thereof, which may become a problem in practical use. It is also possible to mix a medicine such as a preventive to an infectious disease, if necessary, with this mixed solution before use.

In order to solidify human-fibrinogen so that it functions as an adhesive, it is essential to mix therewith thrombin "Thrombin-Midori" (produced by Green Cross Corporation), calcium chloride (Japanese Pharmacopoeia calcium chloride) as an activator of the thrombin, and aprotinin (aprotinin injection) as an inhibitor of dissolution of fibrin. The same is the case with a mixed solution of human-fibrinogen and silk-fibroin of the present invention.

If a slight physical stimulus such as vibration by ultrasonic waves is applied to the surface to which an adhesive has been applied, the silk-fibroin in the mixture adequately displays a function of an adhesive. More specifically, the silk-fibroin is quickly separated out and manifests the excellent mechanical properties characteristic of silk-fibroin. Thrombin, calcium chloride and aprotinin are mixed with the mixed solution of human-fibrinogen and silk-fibroin of the present invention by an ordinary method, described hereinbelow.

(1) Application of "Fibrinogen-Midori" and "Thrombin-Midori" as Surgical Adhesive (materials made by Green Cross Corporation)

General Directions

Liquid A (a solution of a mixture of human-fibrinogen and silk-fibroin) and liquid B (a solution of a mixture of thrombin, aprotinin and calcium chloride) are prepared. In applying the adhesive to an adherend surface, either of the following methods is adopted:

(1) wet-on-wet coating: a method of first applying liquid A to the adherend surfaces, then applying liquid B, bonding the adherend surfaces with each other, and fixing them for about 1 minute (if ultrasonic waves are projected, the adhesive displays a strong adhesive force immediately after bonding);

(2) mixing method: a method of mixing a predetermined amount of liquid A and liquid B in a container, applying the mixture to the adherend surfaces (the process from the mixture to the application is preferably finished within 1 to 1.5 minutes, and if the mixture has been gelled, it cannot be used), immediately bonding the adherend surfaces, and fixing them for 1 minute (ultrasonic waves are projected, if necessary).

Quantities of Materials

Ordinarily, 0.1 ml of liquid A (0.1 ml of liquid B) per square centimeter of the adherend surface is used.

Application Range

The adhesive is applicable to the following treatments:
Bonding of endocranium
Shunt of nerve
Shunt of micro-blood vessel
Reinforcement of blood vessel suture
Obturation of tympanic membrane with traumatic coloboma (tear or hole)
Obturation of substitute blood vessel and reinforcement of sutured portion
Bonding of broken portion of liver, portion incised for liver test, and incised portion of gallbladder
Treatment of trauma at the time of cutting out a part of the kidney, rupture of kidney and removal of the prostate
Maintenance of shunt of intestine
Bonding of cutaneous valve
Obturation of atrium of traumatic bone and cartilage portion (especially when the patient is in danger of bleeding)
Bonding of cartilage and bone portion
Reinforcement of suture of tendon
Bonding of pleura in the case of pneumothorax
Occlusion of alveolus after tooth extraction when there is a danger of bleeding
Occlusion of tonsil fossa using collagen fassicular fibers (especially, when the patient is in danger of bleeding), and
Skin grafting in the case of a burn.

The adhesive may also be used merely as a hemostatic.

The invention now being generally described, the same will be better understood by reference to certain specific examples which are included herein for purposes of illustration only and are not intended to be limiting of the invention or any embodiment thereof, unless specified.

EXAMPLE 1

100 g of waste silk was immersed in 5 l of an aqueous solution containing 0.2 wt % of marseilles soap at 80° C. for 1 hour. Thereafter the silk was treated with a sericin decomposing enzyme, papain, to almost completely remove sericin from the silk. The thus-treated silk was thoroughly washed with water and dried to be used as a silk-fibroin material.

50 g of the silk-fibroin material was immersed in 500 ml of water with 4.5 mol of lithium bromide dissolved therein, and was completely dissolved in the solution at 50° C. in 5 hours. After the inclusions were filtered out, the filtrate was charged into a cellophane tube, and dialyzed for 2 days to remove lithium bromide. Since the fibroin concentration immediately after the dialysis was as low as about 5 wt %, the aqueous fibroin solution accommodated in the cellophane tube was allowed to stand in the air for 2 days to concentrate it by air drying so as to have a concentration of 8 wt %.

Preparation of liquid A 12 ml of Japanese Pharmacopoeia distilled water for injection was poured into 1 g of Fibrinogen-Midori (produced by Green Cross Corporation), dissolved at 32° to 36° C. in 30 seconds, and the concentration was adjusted to 6 % in the end.

Preparation of liquid B 1.2 ml of a mixed solution of 1 ml of liquid Conclyte Ca (Japanese Pharmacopoeia calcium chloride 0.5M), 7.5 ml of distilled water for injection and 1 ml of Trasylol 40000 KIE (produced by Bayer, West Germany) was added to 500 units of Thrombin-Midori (produced by Green Cross Corporation).

Preparation of liquid silk-fibroin (hereinunder referred to as "liquid F")

The above described 8% silk-fibroin was dissolved in distilled water so as to have a concentration of 6% as liquid A.

Bonding test

A 20 mm-wide strip of regenerated collagen film "Meipc" (registered trade mark, produced by Meiji Seika Kaisha Ltd.) was used. 0.09 ml a mixture of liquid A and liquid F (0.05 ml of liquid A and 0.05 ml of liquid F were gently mixed) was applied to both adherend surfaces in such a manner as to have an adherend area of 20 mm×2 mm, and was left to stand for 30 to 60 seconds. Thereafter, the same amount of liquid B as the amount of liquid A was applied to the adherend surfaces coated with liquid A, and the adherend surfaces were immediately bonded by lightly pressing and fixing them for 60 seconds.

Measurement of adhesive force

After the sample was allowed to stand for 24 hours at room temperature, the adhesive strength (g/cm²) under shear was obtained by carrying out the shearing test on the bonded surface at a temperature of 24° C. and a humidity of 65% by a Tensilon type all-purpose tensile testing machine UTM produced by Toyo Sokuki K.K.

EXAMPLE 2

In the bonding test in Example 1, liquid A was used in place of the mixture of liquid A and liquid F.

EXAMPLE 3

In the bonding test in Example 1, immediately after bonding the adherend surfaces, an oscillator rod of an ultrasonic crushing apparatus SONICATOR AUS-01 produced by Ultrasonic Industry Ltd. was lightly pressed against the bonded surface for 60 seconds.

EXAMPLE 4

In the bonding test in Example 3, 0.09 ml of a mixture of 0.05 ml of liquid A and 0.05 ml of 0.1N aqueous calcium chloride solution with 6% silk-fibroin dissolved therein was used in place of the mixture of liquid A and liquid F.

EXAMPLE 5

In the bonding test in Example 4, 0.09 ml of a mixture of 0.09 ml of liquid A and 0.03 ml of 0.1N aqueous calcium chloride solution with 6% silk-fibroin dissolved therein was used.

EXAMPLE 6

In the bonding test in Example 4, 0.09 ml of a mixture of 0.03 ml of liquid A and 0.09 ml of 0.1N aqueous calcium chloride solution with 6% silk-fibroin dissolved therein was used.

EXAMPLE 7

In the bonding test in Example 3, 0.09 ml of liquid F alone was used in place of the mixture of liquid A and liquid F.

EXAMPLE 8

In the bonding test in Example 4, 0.09 ml of a mixture of 0.09 ml of liquid A and 0.06 ml of 0.1N aqueous calcium chloride solution with 6% silk-fibroin dissolved therein was used.

EXAMPLE 9

In the bonding test in Example 3, liquid prepared by the following method was used in place of liquid F; a silk gland was removed from antheraea pernyi, washed with distilled water immediately, dried to be used as a silk-fibroin at room temperature, and the dried silk was dissolved in distilled water so as to have a concentration of 6 wt %.

The adhesive strengths under shear of the samples in Examples 1 to 9 are shown in the following table.

| Example | Mixing Ratio Liquid A | Mixing Ratio Liquid F | Treatment for Bonding | Adhesive Strength Under Shear (g/cm²) |
|---|---|---|---|---|
| 1 | 1 | 1 | | 1,671 |
| 2 | 1 | — | | 792 |
| 3 | 1 | 1 | Ultrasonic treatment | 1,784 |
| 4 | 1 | 1 | 0.1 N aqueous calcium solution, Ultrasonic treatment | 1,826 |
| 5 | 3 | 1 | 0.1 N aqueous calcium solution, Ultrasonic treatment | 1,380 |
| 6 | 1 | 3 | 0.1 N aqueous calcium solution, Ultrasonic treatment | 837 |
| 7 | — | 1 | 0.1 N aqueous calcium solution, Ultrasonic treatment | 84 |
| 8 | 3 | 2 | 0.1 N aqueous calcium solution, Ultrasonic treatment | 2,014 |
| 9 | 1 | 1 | 0.1 N aqueous calcium solution, Ultrasonic treatment | 1,630 |

The present invention is characterized in that mixing of silk-fibroin with human-fibrinogen brings about the effect of not only increasing the adhesive strength under shear but also toughness in adhesion. Referring to FIG.

1, which shows the comparison between the strength-elongation curve of the test of the adhesive strength under shear in Example 2 (human-fibrinogen alone) and those in Example 4 (human-fibrinogen/silk-fibroin=1/1) and Example 8 (human-fibrinogen/silk-fibroin=3/2), the shear strengths of the samples containing silk fibroin are gradually reduced. The adherend surfaces are not sheared at a stroke. That is, the silk-fibroin provides adhesion with toughness.

Advantages of the Invention

The present invention provides an adhesive suitable for surgery, which has greater compatibility with a living organism and adhesiveness than a conventional one, by producing a solution of a mixture of human-fibrinogen and silk-fibroin. This adhesive enables surgical operations to be carried out faster and even makes operations possible which have been previously impossible, because of problems in the bonding surface. Thus, the adhesive of the present invention is expected to greatly contribute to the progress of medical techniques which are socially demanded in part due to increasing numbers of aged persons.

Many modifications and variations of the present invention are possible in light of the above teachings. Therefore, it is to be understood that within the scope of the appended claims, the invention may be practiced otherwise than as specifically described.

What is claimed as new and desired to be secured by Letters Patent of the United States is:

1. An adhesive comprising a mixture of human-fibrinogen and silk-fibroin.

2. An adhesive according to claim 1, wherein the content of said silk-fibroin in said mixture is 5 to 90% by weight.

3. An adhesive according to claim 1, wherein said silk-fibroin is obtained from domestic silk or wild silk, or a mixture thereof.

4. An adhesive according to claim 1, which is sterile, so that it is applicable as a surgical adhesive.

* * * * *